United States Patent [19]

Karlsson et al.

[11] Patent Number: 4,514,257

[45] Date of Patent: Apr. 30, 1985

[54] METHOD OF MEASURING FINES IN PULP SUSPENSIONS

[75] Inventors: Håkan I. Karlsson, Åkersberga; Jan G. T. Pettersson, Täby, both of Sweden

[73] Assignee: Svenska Traforskningsinstitutet, Sweden

[21] Appl. No.: 357,476

[22] Filed: Mar. 12, 1982

[30] Foreign Application Priority Data

Mar. 19, 1981 [SE] Sweden ................. 8101741

[51] Int. Cl.³ ............... G01N 15/00; G01N 21/00; G01N 21/31
[52] U.S. Cl. ..................... 162/49; 356/335; 356/411; 356/418; 356/442; 162/254
[58] Field of Search ............... 162/49, 254, 263, 198; 356/335, 407, 410, 411, 418, 442

[56] References Cited

U.S. PATENT DOCUMENTS

| 3,089,382 | 5/1963 | Hecht et al. ............... 356/418 |
| 3,153,722 | 10/1964 | Bayly et al. . |
| 3,211,961 | 10/1965 | Bayly et al. . |
| 3,614,450 | 10/1971 | Hill et al. . |
| 3,816,241 | 6/1974 | Blume ............... 162/254 |
| 3,902,812 | 9/1975 | Honkawa ............... 356/418 |
| 4,078,863 | 3/1978 | Eriksson et al. . |
| 4,136,959 | 1/1979 | Honkawa et al. ............... 356/407 |
| 4,318,180 | 3/1982 | Lundqvist et al. ............... 162/263 |

FOREIGN PATENT DOCUMENTS

| 2004087 | 8/1970 | Fed. Rep. of Germany . |
| WO81/00622 | 5/1981 | PCT Int'l Appl. . |
| 305757 | 11/1968 | Sweden . |
| 387172 | 8/1976 | Sweden . |
| 2046898 | 11/1980 | United Kingdom . |
| 0739165 | 6/1980 | U.S.S.R. ............... 162/254 |

Primary Examiner—Steve Alvo
Attorney, Agent, or Firm—Lerner, David, Littenberg, Krumholz & Mentlik

[57] ABSTRACT

Methods of measuring the crill content of pulp suspensions are disclosed. The methods include passing a first light radiation, preferably ultraviolet light, having a wavelength comparable to the particle diameter of the crill, through the pulp suspension, passing a second light radiation having a wavelength longer than the first wavelength but shorter than the mean pulp diameter through the pulp suspension, collecting both light radiations after they have transilluminated the pulp suspension, and measuring absorbencies for both of these collected light radiations so that the crill content can be determined therefrom.

10 Claims, 3 Drawing Figures

METHOD OF MEASURING FINES IN PULP SUSPENSIONS

FIELD OF THE INVENTION

The present invention relates to methods for measuring the content of fines (or crill) in pulp suspensions.

BACKGROUND OF THE INVENTION

In order to obtain pulps having specified desirable properties from the beating or refining of pulps, it is necessary to control the beating process. In order to obtain such control, so-called freeness testers are generally used to determine the freeness or drainage property of the pulp. To obtain the automatic control of such beating, however, such testers are only used to a small extent, since the freeness does not constitute an unambiquous measurement of the quality and operability of the pulp. The dewatering of the pulp, and thus the measure of its freeness, depends by its very nature on a number of factors, such as the fines and fiber content thereof.

SUMMARY OF THE INVENTION

In accordance with the present invention, methods for measuring the content of crill particles in a suspension of pulp fibers have now been discovered. In such suspensions in which the crill particles have a first mean particle diameter and the pulp fibers have a second mean particle diameter, the first mean particle diameter being substantially less than the second mean particle diameter, the content of crill particles is determined in accordance herewith by passing a first light radiation having a first wavelength through the pulp suspension, the first wavelength corresponding to the first mean particle diameter, passing a second light radiation having a second wavelength through the pulp suspension, the second wavelength being longer than the first wavelength but shorter than the second mean particle diameter, collecting the first and second light radiations after they have passed through the pulp suspension, measuring first and second absorbencies for the first and second collected light radiations, respectively, and determining the content of the crill particles in the pulp suspension from the first and second absorbencies.

In accordance with the preferred embodiment of the method of the present invention, determination of the content of crill particles in the pulp suspension is made by determining the difference between the first and second absorbencies in order to measure the surface of the crill particles in the pulp suspension.

In accordance with another embodiment of the method of the present invention, determination of the content of the crill particles in the pulp suspension is made by determining the ratio between the first and second absorbencies, in order to measure the proportion of the crill particles in the pulp suspension. The mean diameter of the fibers may be measured separately and utilized to correct the ratio between the first and second absorbencies.

In accordance with a preferred embodiment of the method of the present invention, in which the pulp suspension includes dissolved substances, the crill particles and pulp fibers are separated from the pulp suspension including those dissolved substances so to form a pulp-free pulp suspension, the first and second light radiations are passed through the pulp-free pulp suspension and collected thereafter, and first and second pulp-free absorbencies are measured for the first and second collected light radiations, respectively, so that the first and second absorbencies can be corrected employing the first and second pulp-free absorbencies.

In accordance with a preferred embodiment of the method of the present invention in which the crill particles include free crill particles and crill particles partly bound to the fibers, the free crill particles are separated from the pulp suspension so to form a free crill suspension. Then the content of bound crill particles can be measured in the pulp suspension and the content of free crill particles in the free crill suspension. Alternatively first and second free crill absorbencies can be measured in the free crill suspension and utilized to correct the first and second absorbencies in order to determine the content of free and bound crill in the pulp suspension.

In accordance with a preferred embodiment of the method of the present invention, a third light radiation having a third wavelength is passed through the pulp suspension, the third wavelength being longer than the first wavelength and shorter than the second wavelength, the third light radiation is collected after it has passed through the pulp suspension, and a third absorbency for the collected third light radiation is measured, so that the content of crill in the pulp suspension can be determined from the first, second and third absorbencies. In a preferred embodiment, the third light radiation comprises a plurality of third light radiations, each having a wavelength longer than the first wavelength but shorter than the second wavelength.

In accordance with another embodiment of the present invention, the method includes determining the freeness of the pulp suspension and combining the content of crill particles in the pulp suspension with the freeness of the pulp suspension in order to measure the mechanical properties of the pulp. In a preferred embodiment, determination of the freeness of the pulp suspension comprises dewatering the pulp suspension.

It can thus be seen that this invention permits the surface of the proportion of fines (referred to herein as crill) content in the beaten material to be determined. From this determination, the relative crill content, i.e., the proportion of crill in the pulp suspension, can be determined. By then combining the proportion of crill particles with a measure of drainage properties of the pulp, which is preferably measured by a high-speed dewatering method, it has now been found possible to calculate the mechanical properties of the fibers by means of a mathematical model. When paper qualities and operability properties of the pulp were related to the proportion of crill and said calculated mechanical properties of the fibers, distinct interrelationships could be observed. From these interrelationships it was thus possible to determine optimum operating conditions, and they can be further utilized for automatically controlling the beating process. During the beating of cellulosic materials, the fibers are affected in different ways. Fibrillation, for example, occurs, i.e., the fibrils of the fiber walls are exposed to a greater or lesser degree. These fibrillary particles are called crill particles. Entirely separated fibrils are called free crill and exposed but not entirely separated fibrils are called bound crill. The crill particles have a diameter which is about one hundred times smaller than the fiber diameter.

These crill particles also have a very large surface area in relation to their weight and, therefore, affect the dewatering properties of the pulp to a high degree especially the free crill content, as well as the porosity and mechanical properties of the paper products produced therefrom.

According to the present invention, measurements utilizing the capacity of the crill particles to absorb and diverge light rays (absorbency) at different wavelengths is used to determine the crill content in the pulp.

This invention may be more fully understood with reference to the following detailed description, referring specifically to the drawings, in which.

DETAILED DESCRIPTION

Figure 1:
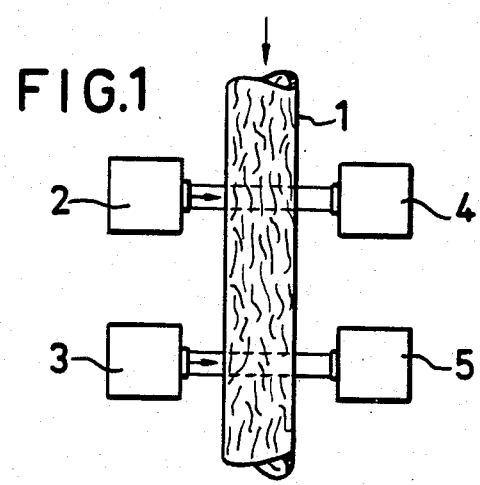
FIG. 1 shows a schematic representation of the principle of measurement according to the present invention, using a pair of light sources.
Figure 2:
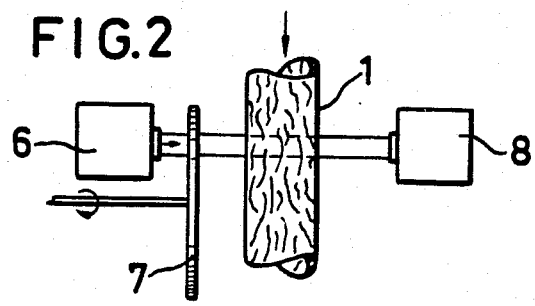
FIG. 2 shows an alternative schematic representation of the principle of measurement according to the present invention, using a single light source.

Referring to FIG. 1, a sample of the pulp to be measured is passed through a passageway 1, which is preferably in the form of a glass cell. As shown in FIG. 1, the pulp is transilluminated by light of different wavelengths from two light sources, 2 and 3, respectively. The transmitted light, after passing therethrough, is collected by two light detectors, 4 and 5, respectively. According to the embodiment shown in FIG. 2, a light source 6 and a rotary filter 7 are used which alternatively permit the passage of light of two different wavelengths. The transmitted light is collected by a light detector 8 in this case.

While the light detectors, 4, 5 and 8 collect only the transmitted light, they are nevertheless arranged so as to emit an output signal corresponding to the absorbency, i.e., that part of the light radiation which is absorbed and diverged by the pulp. The relationship between the absorbency (A) and the transmittance (T) can be expressed as follows:

$$A = \log 1/T$$

Figure 3:
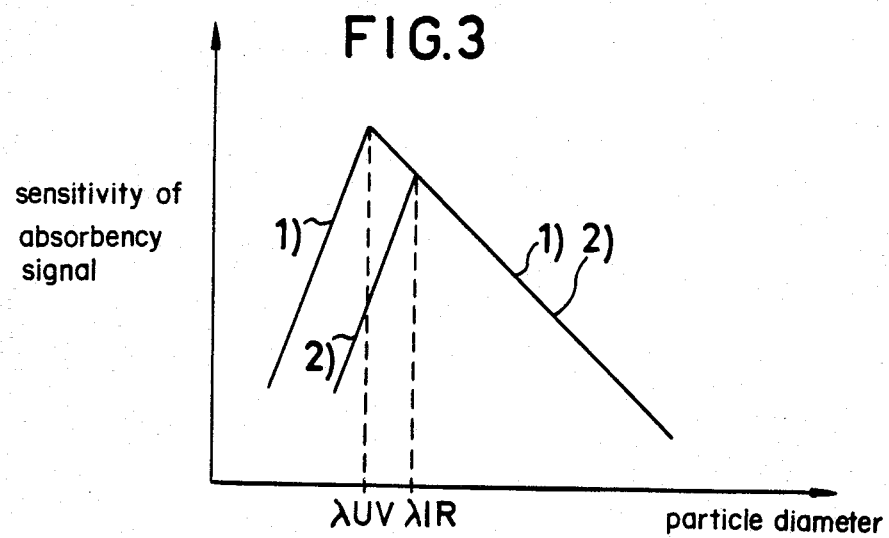
FIG. 3 shows a graphical representation of absorbency versus particle diameter at a constant particle concentration at two particular wavelengths of light.

The absorbency (A) of particles for light radiation of a specified wavelength depends upon the particle diameter. The absorbency at a constant particle concentration, e.g. measured in mg/l, has a maximum when the particle diameter is about the same size as the wavelength of the light. FIG. 3 shows this relationship in a diagram where the sensitivity ($v$) of the absorbency signal is shown as a function of the particle diameter, in logarithmic scales. Curve (1) refers to ultraviolet light with a wavelength $\lambda_{UV}$, and curve (2) refers to infrared light with a wavelength $\lambda_{IR}$. The absorbency (A) is a product of the sensitivity ($v$) and the particle concentration (c), as follows:

$$A = v \cdot C$$

This implies that even when the concentration of particles having a specified diameter is low, the absorbency can still be considerable when the light ray has a wavelength on the same order of magnitude as the particle diameter.

In connection with the present invention, this implies that the wavelengths of the light rays transilluminating the pulp shall be as follows. One (the first) light ray shall have a wavelength of the same magnitude as the diameter of the crill particles in the pulp. In a preferred measuring instrument, actually utilized ultraviolet light with a narrow wavelength range of about 0.254 μm can be used. The second light radiation as a longer wavelength, but it also has a shorter wavelength than the diameter of the fibers in the pulp, and preferably from about 0.5 to about 5 μm. In practice, the transmission conditions in water limit the applicable interval. In a preferred measuring instrument actually utilized, infrared light with a narrow wavelength range of about 0.940 μm can be used.

By utilizing this method, the crill particles have a relatively great influence on the absorbency at the first wavelength, even though the concentration of crill particles is very low relative to the concentration of fibers, as measured in mg/l. At the second wavelength, however, the influence of the crill particles on the absorbency is substantially smaller, while the influence of the fibers on the absorbency remains sustantially unchanged. The difference between these two absorbency values thus constitutes a measure of the content of crill particles in the pulp. The quotient between the two absorbency values yields a measure of the crill proportion of the pulp, i.e., the proportion of crill in the pulp. It is also possible to use the absorbency values so obtained to form other linear combinations.

In measuring the crill proportion the result is changed if the mean diameter of the fibers is changed, since the absorbency is inversely proportioned to the diameter of the fibers. In order to compensate for that, the mean diameter of the fibers can be measured separately and utilized for correction of the quotient between the two absorbency values as mentioned above. This will give a crill proportion which is independent of the diameter of the fibers.

In connection with such fibers and fibrous materials in the pulp suspensions, the absorbency can also be influenced by dissolved substances in the pulp suspension. In order to prevent this from interfering with the measuring of the crill content, the influence of these dissolved substances on the absorbency must be separately determined, so that the absorbency value for the pulp suspension can be corrected. This is preferably carried out by separating solid materials from the pulp sample, whereafter the above-described absorbency measurement can be carried out only on the liquid. The resulting value is then subtracted from the absorbency values determined for the entire pulp sample.

In the methods described above light radiation of two wavelengths is used for determining the crill content. This is per se sufficient, but it is also possible according to this invention to use one or several more wavelengths, and to determined corresponding absorbencies therefor. In this manner, it can be possible, for example, to detect the size distribution of the crill particles in greater detail. The invention, of course, is not restricted to the examples set forth above, but can be varied within the scope of the invention idea.

It will be understood that the embodiment described herein is merely exemplary and that a person skilled in the art may make many variations and modifications without departing from the spirit and scope of the invention. All such modifications and variations are intended to be included within the scope of the invention as defined in the appended claims.

What is claimed is:

1. A method of measuring the content of crill particles in a suspension of pulp fibers wherein said crill particles have a first mean particle diameter and said pulp fibers have a second mean particle diameter, said first mean particle diameter being substantially less than said second mean particle diameter, said method comprising passing a first light radiation having a first wavelength through said pulp suspension, said first wavelength being of the same magnitude as said first mean particle diameter, passing a second light radiation having a second wavelength through said pulp suspension, said second wavelength being longer than said first wavelength but shorter than said second mean particle diameter, collecting said first and second light radiations after they have passed through said pulp suspension, measuring first and second absorbencies for said first and second collected light radiations, respectively, and determining the content of said crill in said pulp suspension from said first and second absorbencies.

2. The method of claim 1 wherein said determination of said content of said crill particles in said pulp suspension comprises determining the difference between said first and second absorbencies so as to measure the surface of said crill particles in said pulp suspension.

3. The method of claim 1 wherein said determination of said content of said crill particles in said pulp suspension comprises determining the ratio between said first and second absorbencies so as to measure the proportion of said crill particles in said pulp suspension.

4. The method of claim 3 wherein the mean diameter of the fibers is measured separately and utilized to correct the ratio between said first and second absorbencies.

5. The method of claim 1 wherein said pulp suspension includes dissolved substances, and including separating said crill particles and said pulp fibers from said pulp suspension including said dissolved substances so as to produce a pulp-free pulp suspension, passing said first and second light radiations through said pulp-free pulp suspension, collecting said first and second light radiations after they have passed through said pulp-free pulp suspension, measuring first and second pulp-free absorbencies for said first and second collected light radiations, respectively, and correcting said first and second absorbencies utilizing said first and second pulp-free absorbencies.

6. The method of claim 1 wherein said crill particles include free crill particles and crill particles partly bound to the fibers, and including separating said free crill particles in a suspension from said pulp suspension and measuring the content of bound crill particles in said pulp suspension and the content of free crill particles in said free crill suspension.

7. The method of claim 1 wherein said crill particles include free crill particles and crill particles partly bound to the fibres, and including separating said free crill particles in a suspension from said pulp suspension, passing said first and second light radiations through said free crill suspension, collecting said first and second light radiations after they have passed through said free crill suspension, measuring first and second free crill absorbencies for said first and second collected light radiations, respectively, and correcting said first and second absorbencies utilizing said first and second free crill absorbencies in order to determine the content of free and bound crill in said pulp suspension.

8. The method of claim 1 wherein said first light radiation comprises ultraviolet light radiation and said second light radiation comprises infrared light radiation.

9. The method of claim 1 including passing a third light radiation having a third wavelength through said pulp suspension, said third wavelength being longer than said first wavelength and shorter than said second wavelength collecting said third light radiation after it has passed through said pulp suspension, measuring a third absorbency for said collected third light radiation, and determining the content of said crill particles in said pulp suspension from said first, second and third absorbencies.

10. The method of claim 9 wherein said third light radiation comprises a plurality of third light radiations, each having a wavelength longer than said first wavelength and shorter than said second wavelength.

* * * * *